(12) United States Patent
Rao et al.

(10) Patent No.: US 12,236,593 B2
(45) Date of Patent: Feb. 25, 2025

(54) SYSTEM AND METHOD FOR AUTOMATIC DETECTION AND CORRECTION OF ANATOMY, VIEW, ORIENTATION AND LATERALITY IN X-ray IMAGE FOR X-ray IMAGING SYSTEM

(71) Applicant: GE Precision Healthcare LLC, Wauwatosa, WI (US)

(72) Inventors: Gireesha Chinthamani Rao, Pewaukee, WI (US); Ravi Soni, San Ramon, CA (US); Gopal B. Avinash, Concord, CA (US); Poonam Dalal, Brookfield, WI (US); Beth A. Heckel, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 253 days.

(21) Appl. No.: 17/975,867

(22) Filed: Oct. 28, 2022

(65) Prior Publication Data

US 2023/0169649 A1 Jun. 1, 2023

Related U.S. Application Data

(60) Provisional application No. 63/283,344, filed on Nov. 26, 2021.

(51) Int. Cl.
*G06T 7/70* (2017.01)
*G06T 3/60* (2024.01)
*G06T 7/00* (2017.01)

(52) U.S. Cl.
CPC .............. *G06T 7/0012* (2013.01); *G06T 3/60* (2013.01); *G06T 7/70* (2017.01);
(Continued)

(58) Field of Classification Search
CPC .......... G06T 7/0012; G06T 7/70; G06T 3/60; G06T 2207/10116; G06T 2207/20021; G06T 2207/30004; G06T 2207/30168
See application file for complete search history.

(56) References Cited

U.S. PATENT DOCUMENTS 11,776,150 B2 * 10/2023 Younis ................ G06F 18/2431
2021/0166351 A1 6/2021 Younis et al.
(Continued)

FOREIGN PATENT DOCUMENTS

EP 3714792 A1 9/2020

OTHER PUBLICATIONS

EP application 22207480.9 filed Nov. 15, 2022—extended Search Report issued Apr. 21, 2023; 10 pages.
(Continued)

*Primary Examiner* — David P Porta
*Assistant Examiner* — Fani Polyzos Boosalis
(74) *Attorney, Agent, or Firm* — Boyle Fredrickson S.C.

(57) ABSTRACT

An artificial intelligence (AI) X-ray image information detection and correction system is employed either as a component of the X-ray imaging system or separately from the X-ray imaging system to automatically scan post-exposure X-ray images to detect various types of information or characteristics of the X-ray image, including, but not limited to, anatomy, view, orientation and laterality of the X-ray image, along with an anatomical landmark segmentation. The information detected about the X-ray image can then be stored by the AI system in association with the X-ray image for use in various downstream X-ray system workflow automations and/or reviews of the X-ray image.

19 Claims, 4 Drawing Sheets

(52) U.S. Cl.
CPC .............. *G06T 2207/10116* (2013.01); *G06T 2207/20021* (2013.01); *G06T 2207/30004* (2013.01); *G06T 2207/30168* (2013.01)

(56) References Cited

U.S. PATENT DOCUMENTS

2021/0212648 A1   7/2021   Bailey, Sr.
2021/0212650 A1   7/2021   Wang

OTHER PUBLICATIONS

Ivo M. Baltruschat el al., Orientation Regression in Hand Radiographs: A Transfer Learning Approach, Feb. 2018.
Khaled Younis et al., Leveraging Deer Learning Artificial Intelligence in Detecting the Orientation of Chest X-ray Images, Sep. 2019.

* cited by examiner

SYSTEM AND METHOD FOR AUTOMATIC DETECTION AND CORRECTION OF ANATOMY, VIEW, ORIENTATION AND LATERALITY IN X-ray IMAGE FOR X-ray IMAGING SYSTEM

CROSS-REFERENCE TO RELATED APPLICATIONS

The present application claims priority from U.S. Provisional Patent Application Ser. No. 63/283,344, filed on Nov. 26, 2021, the entirety of which is expressly incorporated by reference herein for all purposes.

FIELD OF THE DISCLOSURE

The present disclosure relates to X-ray imaging systems, and more particularly to X-ray imaging systems including ancillary image processing systems to improve workflow and quality of images produced by the X-ray system.

BACKGROUND OF THE DISCLOSURE

A number of X-ray imaging systems of various designs are known and are presently in use. Such systems are generally based upon generation of X-rays that are directed toward a subject of interest. The X-rays traverse the subject and impinge on a detector, for example, a film, an imaging plate, or a portable cassette. The detector detects the X-rays, which are attenuated, scattered or absorbed by the intervening structures of the subject. In medical imaging contexts, for example, such systems may be used to visualize the internal structures, tissues and organs of a subject for the purpose screening or diagnosing ailments.

With regard to the X-ray images produced by the X-ray systems, in order to enable a radiologist or other medical practitioner to review the produced X-ray images in an efficient manner, the X-ray images must be labeled by the technician or another individual to properly identify the subject of the X-ray image. This identification includes reviewing the X-ray image to determine the anatomy that is present in the image, the view and orientation of the anatomy shown in the image, as well as the laterality of the anatomy shown in the image, if applicable. The information regarding each of these aspects of the X-ray image is entered and stored in association with the X-ray image in the form of DICOM tags, with each tag providing information on an aspect of the X-ray image.

While the process of reviewing the X-ray image and to enter all of the DICOM tag/data concerning the anatomy, view orientation and laterality makes subsequent review of the X-ray images very efficient for the radiologist, the procedure for the review and data entry of the DICOM tags requires a significant amount of time on the part of the technician.

In addition, on certain occasions the technician can enter an incorrect DICOM tag with regard to a particular X-ray image. This creates an issue with regard to the review of the X-ray image, as initially the X-ray image may not be readily located due to the incorrect identifying information (DICOM tag(s)) stored in association with the X-ray image, and subsequently the incorrect information must be removed and replaced with a proper DICOM tag for the X-ray image. Each of these results of an incorrect DICOM tag being entered require significant time to both discover and correct, causing a significant inefficiency in the review process for the X-ray image.

Further, even when there are no issues with regard to the DICOM tags for an X-ray image, many times the orientation/rotation of the anatomy within the X-ray image must be adjusted in order to provide the desired view of the anatomy within the X-ray image. This is accomplished during the initial review of the post-exposure X-ray image and also can require a significant amount of time in order to re-position/re-orient the anatomy in the X-ray image as required for the particular view of the anatomy represented in the X-ray image.

Therefore, it is desirable to develop a system and method for automatically detecting the various attributes of a post-exposure X-ray image that minimizes errors concerning the information stored in association with the X-ray image and/or for automatically correcting the anatomy orientation/rotation within the post-exposure image that overcomes these limitations of the prior art.

SUMMARY OF THE DISCLOSURE

According to one aspect of an exemplary embodiment of the disclosure, an artificial intelligence (AI) X-ray image information detection and correction system is employed either as a component of the X-ray imaging system or separately from the X-ray imaging system to automatically scan post-exposure X-ray images to detect various types of information or characteristics of the X-ray image, including, but not limited to, anatomy, view, orientation and laterality of the X-ray image, along with an anatomical landmark segmentation. The information detected about the X-ray image can then be stored by the AI system in association with the X-ray image for use in various downstream X-ray system workflow automations and/or reviews of the X-ray image.

According to another aspect of an exemplary embodiment of the disclosure, the AI information detection and correction system can determine errors in the orientation or rotation of the anatomy in the X-ray image relative to the view for the X-ray image. Though the rotation precision requirements are different for different anatomies and/or views, instead of having multiple networks for each view, the single AI information detection system can support all views and all anatomies with variable rotation supports to automatically adjust the rotation of the anatomy within the X-ray image to match the desired orientation for the view of the anatomy in the X-ray image.

According to still another aspect of an exemplary embodiment of the disclosure, the AI information detection system provides a number of outputs with regard to the X-ray image analyzed by the AI information detection system that can be referenced against one another as a self-check concerning the validity/accuracy of the review/predictions made by the AI information detection system According to another exemplary embodiment of the disclosure, an X-ray system includes an X-ray source, an X-ray detector positionable in alignment with the X-ray ray source, and a processing unit operably connected to the X-ray source and the X-ray detector to produce X-ray images from data transmitted from the X-ray detector, wherein the processing unit includes an X-ray image information detection system configured to detect information regarding at least one of an anatomy, a laterality, an orientation and a rotation of an anatomy represented within the X-ray image using the X-ray image information detection system.

According to still another exemplary embodiment of the present disclosure, a method of determining information present in an X-ray image includes the steps of providing an X-ray system having an X-ray source, an X-ray detector positionable in alignment with the X-ray ray source and a processing unit operably connected to the X-ray source and the X-ray detector to produce X-ray images from data transmitted from the X-ray detector, wherein the processing unit includes an X-ray image information detection system configured to detect an anatomy present in the X-ray images, and one or more of a view, an orientation and/or laterality present in the X-ray images, applying the X-ray image information detection system to the X-ray images, and providing an output from the X-ray image information detection system with information regarding the X-ray image.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Figure 1:
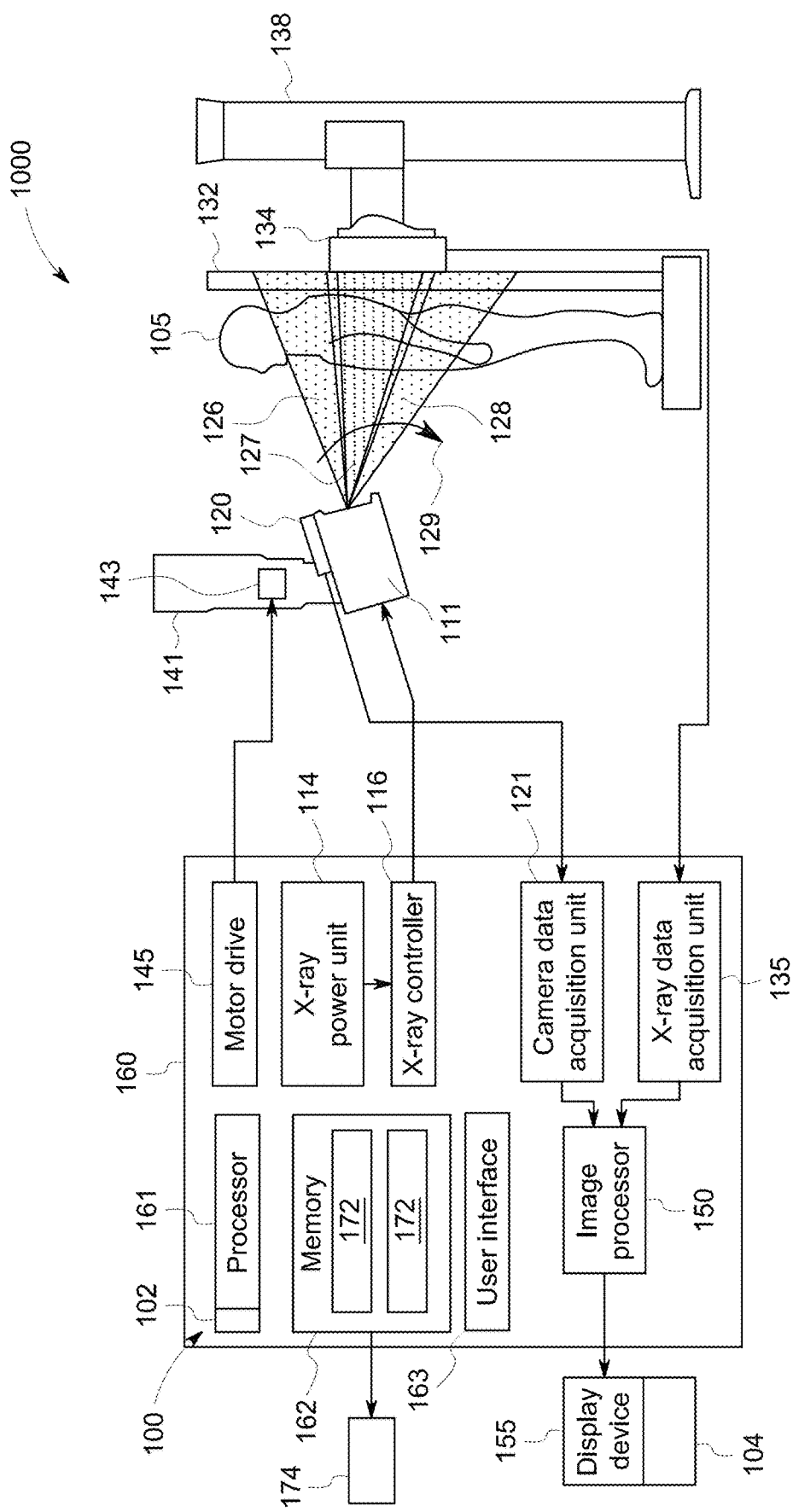
FIG. 1 is a schematic view of an X-ray imaging system employing the AI information detection and correction system according to an exemplary embodiment of the disclosure.

Referring to FIG. 1, a block diagram of an x-ray imaging system 1000 in accordance with one exemplary embodiment of the disclosure is shown. The x-ray imaging system 1000 includes an x-ray source 111 which radiates x-rays, a stand 132 upon which the subject 105 stands during an examination, and an x-ray detector 134 for detecting x-rays radiated by the x-ray source 111 and attenuated by the subject 105. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 160 comprises a processor 161, a memory 162, a user interface 163, a motor drive 145 for controlling one or more motors 143, an x-ray power unit 114, an x-ray controller 116, a camera data acquisition unit 121, an x-ray data acquisition unit 135, and an image processor 150. X-ray image data transmitted from the x-ray detector 134 is received by the x-ray data acquisition unit 135. The collected x-ray image data are image-processed by the image processor 150. A display device 155 communicatively coupled to the operating console 160 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 105. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 145 of the operation console 160 may be communicatively coupled to the one or more motors 143 and configured to control the one or more motors 143. The one or more motors 143 may further be configured to adjust an angular position of the x-ray source 111 to change a field-of-view of the x-ray source 111, as described further herein.

The x-ray power unit 114 and the x-ray controller 116 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject 105 or portion thereof via the collimator.

The x-ray source 111 and the camera 120 may pivot or rotate relative to the support post 141 in an angular direction 129 to image different portions of the subject 105.

Memory 162 stores executable instructions 172 that when executed cause one or more of the processor 161 and the image processor 150 to perform one or more actions.

Example methods that may be stored as the executable instructions 172 are described further herein with regard to an X-ray image information detection system 100 and AI detection and correction system and application 102 of FIGS. 1-4. Memory 162 can also include a storage location 170 in which the X-ray images 104 can be stored or can be operably connected via a suitable wired or wireless connection to a remote electronic storage device or location 174 where the X-ray images 104 and information associated with the X-ray images 104 ca be stored.

Figure 2:
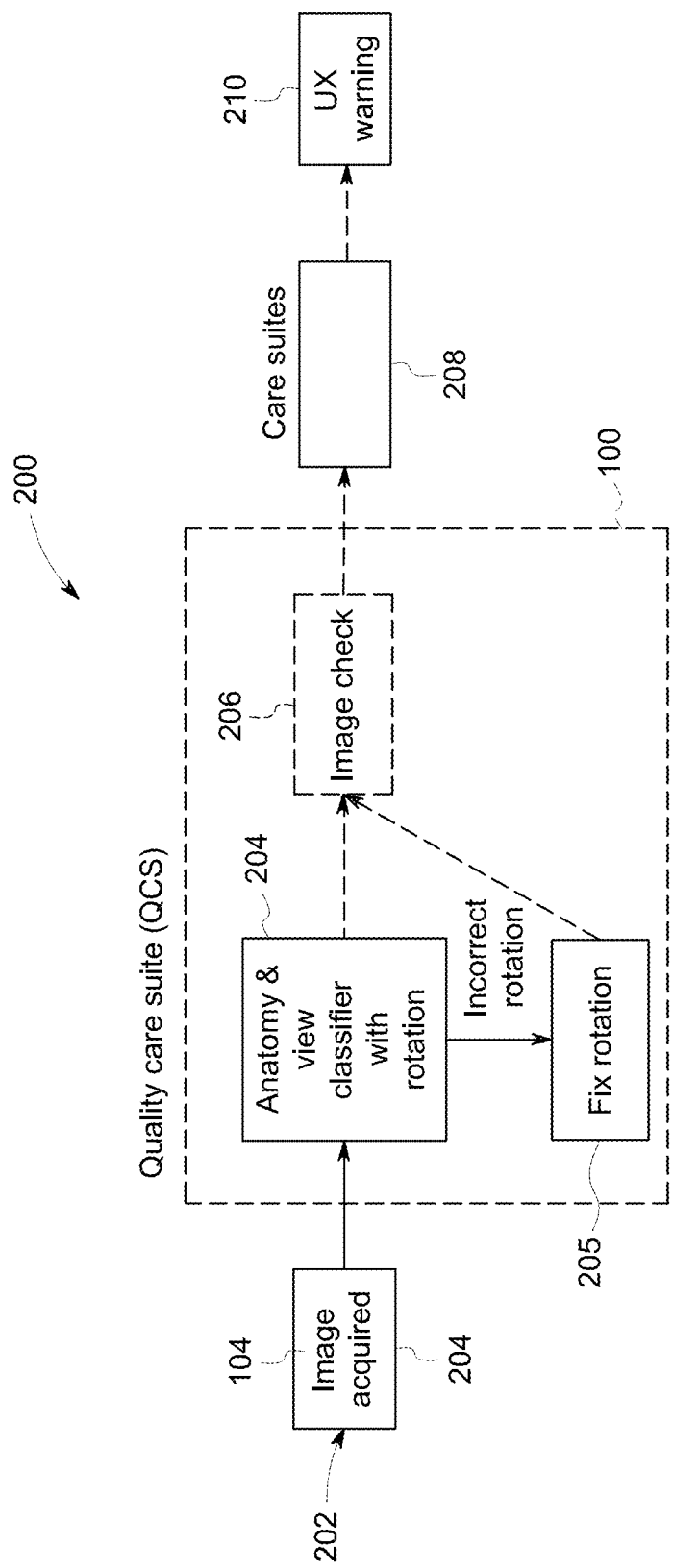
FIG. 2 is a flowchart of a method of operation of the AI information detection and correction system according to an exemplary embodiment of the disclosure.
Figure 3:
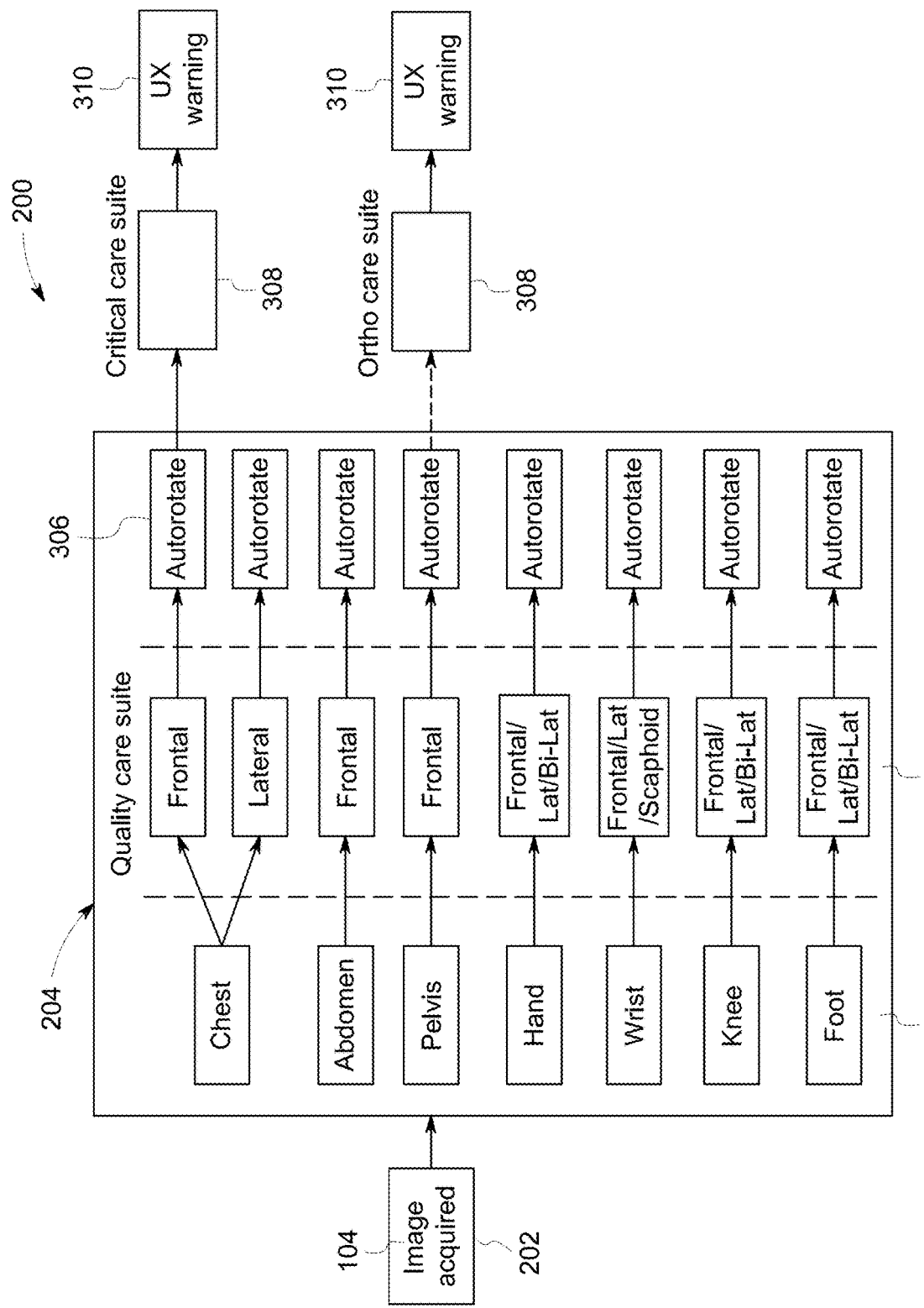
FIG. 3 is a schematic view of the AI information detection and correction system according to another exemplary embodiment of the disclosure.
Figure 4:
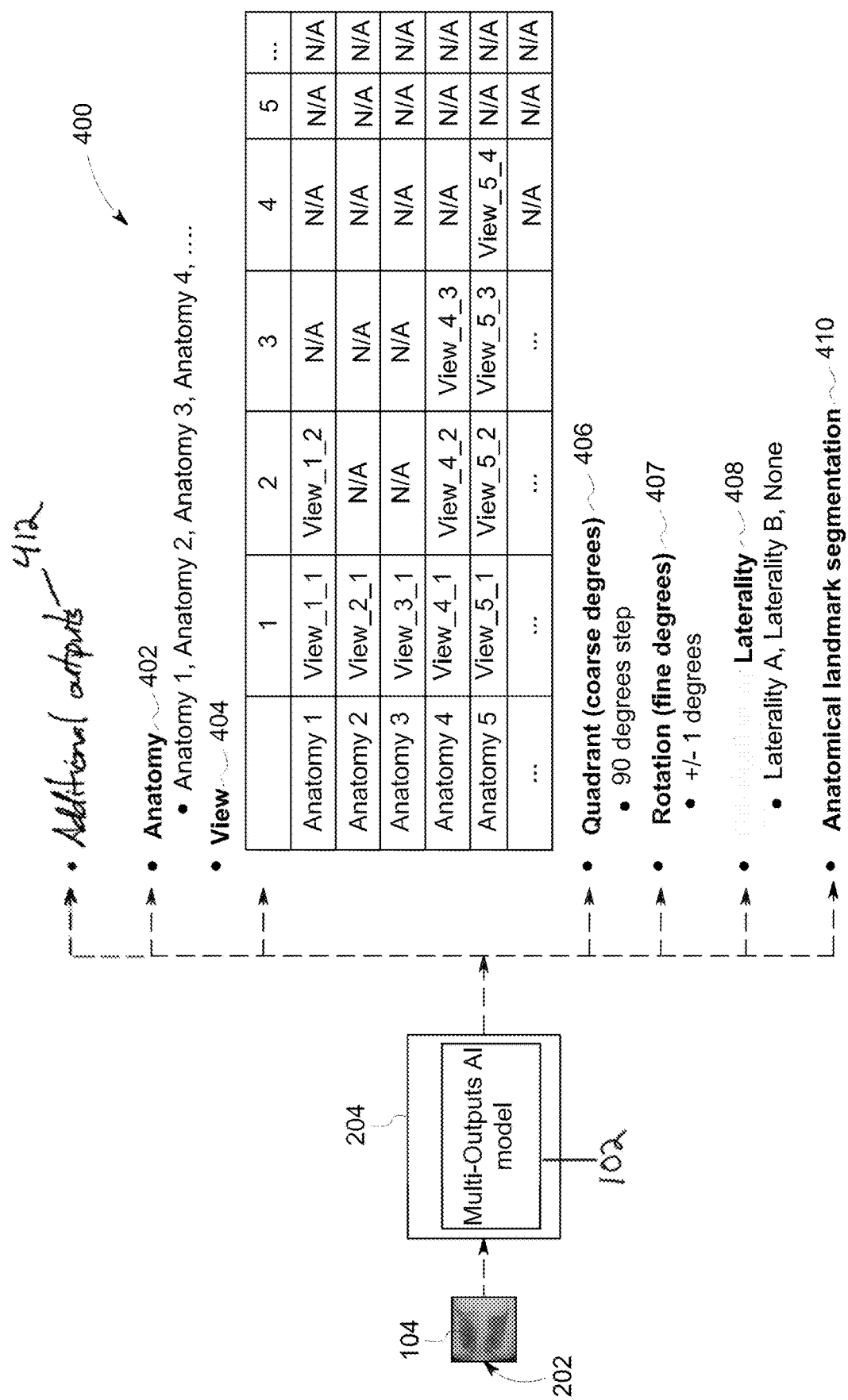
FIG. 4 is a schematic view of the output from the analysis of an X-ray image by the AI information detection and correction system according to an exemplary embodiment of the disclosure.

The processor 161 additionally includes an automatic X-ray image information detection and correction system 100. The automatic X-ray image information detection and correction system 100 is formed by an artificial intelligence (AI) application 102 that can scan and detect various types of information associated with a post-exposure X-ray image 104 (FIGS. 2-4). The AI application 102, which can be a deep learning neural network, for example, is an image-based object detection application that is configured for the detection various attributes of the post-exposure X-ray image 104, such as information regarding the particular anatomy present in the X-ray image 104, view, orientation and/or laterality in the X-ray image 104.

Referring now to FIG. 2, in an exemplary embodiment of a method 200 of operation of automatic X-ray image information detection system 100, initially in block 202 a post-exposure X-ray image 104 is supplied as an input 201 to the system 100. In block 203, also referred to as the image review/quality care suite, the system 100 in block 204 analyzes the image 104 utilizing any suitable image review algorithm(s), process(es) or method(s) employed by the AI application 102 in order to determine the anatomy, view, orientation and/or laterality of the X-ray image 104. In addition, where the AI application 102 determines that there are errors present in any identifying information associated with the image 104, for example, that the X-ray image 104 does not have the proper angular orientation/rotation corresponding to the anatomy and/or view determined by the AI application 102 for the X-ray image 104, the AI application 102 can proceed to block 205 and correct any rotation issues with the X-ray image 104.

The output of the image review analysis in block 204 with any required rotational fix from block 205, is sent to block 206 where one or more various image check algorithms are applied to the X-ray image 104. These downstream algorithms can include, but are not limited to, a positioning check algorithm (e.g., are both lungs visible in a X-ray image 104 of the chest), a pathology check algorithm (e.g., does an X-ray image 104 image obtained for the purposes of evaluating a broken bone include the anatomy including that bone), and an image quality algorithm (e.g., determining if the X-ray image 104 is sufficiently clear with regard to the anatomy illustrated within the image). The image check algorithms applied in block 206 may additionally include an output compatibility check algorithm directed to analyzing the outputs from the AI application 102 in block 204. This compatibility check algorithm is applied to the information determined by the AI application 102 to determine if any components (e.g., view, orientation, laterality, etc.) of the information obtained from the X-ray image 104 by the AI application 102 are incompatible with other components (e.g., a laterality determination for a chest image).

The system 100 then proceeds to block 208 where the information output/analysis results are sent to one or more individual clinical image analysis algorithms/anatomy care suites associated with particular anatomy(ies) determined to be within the X-ray image 104. The anatomy information determined by the AI application 102 in block 204 enables the system 1000 to direct the X-ray image 104 and associated information to an anatomy-specific clinical image analysis algorithm/care suite where the anatomy-specific algorithms are employed to analyze the X-ray image 104 including specific conditions regarding certain specific anatomies, e.g., a pneumothorax analysis regarding an X-ray image 104 of the chest.

From the individual anatomy clinical image analysis algorithms/care suites in block 208, in block 210 the output of the various algorithm analyses in blocks 206 and 208 is provided with any associated warnings determined by one or more of the algorithms applied to the X-ray image 104 in any of blocks 206 or 208 that may require re-analysis of the X-ray image 104.

Referring now to FIG. 3, a more detailed exemplary embodiment of the operation of the image review/quality care suite in block 203 for the automatic X-ray image information detection system 100 is illustrated. After the input of the X-ray image 104 produced by the X-ray system 1000 in block 202, the AI application 102 initially reviews the X-ray image 104 to make a determination of the anatomy represented within the X-ray image 104. In performing this initial analysis portion 302 of the analysis in block 204, the AI application 102 employs an anatomy classifier capable of determining the anatomy present within the X-ray image 104. The classifier can be any suitable algorithm, or an AI, neural network or deep learning image-based object detection and/or recognition method for the determination of the anatomy present in the X-ray image 104. The process employed may additionally involve an automatic anatomy landmark segmentation method whereby the AI application 102 determines the particular anatomy present within the X-ray image 104 through the identification of various learned anatomical landmarks present in various anatomical regions. By identifying these landmarks in the anatomy present in the X-ray image 104, the AI application 102 can identify the anatomy corresponding to those landmarks and digitally label the X-ray image 104 as containing that anatomy. As shown in exemplary embodiment of FIG. 3, the AI application 102 can differentiate anatomical areas in X-ray images 104 that show any of a chest, an abdomen, a pelvis, a hand, a wrist, a knee or a foot.

After identification of the anatomical region present in the X-ray image 104, the AI application 102 proceeds to analysis portion 304 to identify the particular view of the anatomy shown in the X-ray image 104. This is also accomplished utilizing the anatomical landmarks detected in the X-ray image 104 and their orientation with regard to one another within the X-ray image 104. This determination also entails the identification of the orientation and any laterality of the anatomy within the X-ray image 104 by the AI application 102.

Finally, the AI application 102 proceeds to analysis portion 306 where the rotation of the anatomy within the X-ray image 104 is determined. Also, again utilizing the information regarding the anatomical landmarks present in the X-ray image 104, the AI application 102 determines if the position of the anatomy within the X-ray image 104 corresponds to the view of the anatomy previously identified in portion 304. This is accomplished by first determining a coarse position of the anatomy in the image 104, i.e., is the anatomy in the proper 90° quadrant for the detected view, and subsequently any necessary fine position correction, such as an individual degree +/−1° (or more) rotation of the anatomy within the image 104 to match the detected view. This autorotation, is necessary, is performed directly by the AI application 102 with the capability of the user to subsequently verify and/or adjust the rotation of the X-ray image 104.

After the AI application 102 has identified the anatomy in analysis portion 302, identified the view and orientation and/or laterality in analysis portion 304, and corrected the rotation of the anatomy in the X-ray image 104 in analysis portion 306, the AI application 102 can provide this information on the particular image 104 to a specific care suite 308 associated with the anatomy and/or pathology identified by the AI application 102 for the X-ray image 104, as described previously regarding block 208 in the method of FIG. 2, with any subsequent warnings provided in block 310, as also previously described regarding block 210 in FIG. 2.

Looking now at FIG. 4, the output 400 from the AI application 102 that is utilized for the direction of the X-ray image 104 to a particular care suite 308 and that is also provided directly to the specific care suites 308 is illustrated. The output 400 includes an identification of the various anatomies 402 detected by the AI application 102 within the X-ray images 104 input to the AI application 102, an identification 404 of the number and types of views for each detected anatomy, information regarding any coarse 406 or fine 407 identification/auto-rotation/correction of the rotation of the individual image 104, information 408 on the orientation and/or laterality of the anatomy within the image 104, the anatomical landmark segmentation information 410 utilized by the AI application 102 in the process of the identification of these various types of information in the X-ray images 104, and other suitable additional outputs 412 regarding information on the X-ray images 104 provided as inputs to the AI application 102. All of this output 400, is stored by the system 100, such as in electronic information storage 170 or in remote electronic storage device 174 in conjunction or association with the X-ray image 104, in addition to other relevant information, such as patient-identifying information, such that it can be readily accessed during any review of the X-ray image 104. Further, at each stage of the review of an X-ray image 104, the AI application 102 can store the information obtained on the X-ray image 102 in local electronic storage device 170 and/or in remote electronic storage device or location 174 in association with the image 104. In a particular exemplary embodiment, the information determined by the AI application 102 that is stored with respect to the X-ray image 102 in electronic storage 170 and/or 174 can be a number of digital DICOM tags formed using the information determined by the X-ray image detection system 102 that are readable by the various algorithms to facilitate a faster workflow concerning the direction to and analysis of the X-ray image 102 by the algorithms located downstream from the AI application 102 in the workflow.

In this manner, the single AI application 102 can take the place of multiple AI applications each designed to identify a particular anatomical region, consequently simplifying the identification process and the output from the AI application 102 for use in downstream algorithms and for review by providing an optimized "view" branch output categories/table 400 that saves network parameters and number of outputs.

Further, the multiple outputs of the AI application 102 enable the AI application 102 to self-check, or provide a detection of a prediction error by the AI application 102, such as through the use of the compatibility check algorithm described previously, where the multiple outputs for coarse and fine orientation of images allow the detection an AI prediction error, such as any anatomy/view mismatch detection by the AI application 102.

In addition, the AI application 102 is scalable in that the AI application 102 is capable of learning additional anatomical landmarks to identify additional anatomical regions. This enables the AI application 102 to learn and recognize additional anatomical landmarks for other anatomies/anatomical regions present in X-ray images 104, such that the AI application 102 can identify more anatomies, views of those anatomies, orientation, and laterality/direction in the X-ray images 104, as well as any detection problems resulting from the analysis performed by the AI application 102.

Finally, it is also to be understood that the information detection and correction system 100 incorporating the AI application 102 may include the necessary computer, electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor/processing unit/computer and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application(s)/algorithm(s) that adapts the computer/controller to perform the methods disclosed herein may be read into a main memory of the at least one processor from a computer-readable medium. The term "computer-readable medium", as used herein, refers to any medium that provides or participates in providing instructions to the at least one processor of the system 100 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method of determining information present in an X-ray image comprising the steps of:
   providing an X-ray system comprising:
   an X-ray source;
   an X-ray detector positionable in alignment with the X-ray ray source; and
   a processing unit operably connected to the X-ray source and the X-ray detector to produce X-ray images from data transmitted from the X-ray detector, wherein the processing unit includes an X-ray image information detection system configured to detect an anatomy present in the X-ray images, and one or more of a view, an orientation and/or laterality present in the X-ray images;
   applying the X-ray image information detection system to the X-ray images; and
   providing an output from the X-ray image information detection system with information regarding the X-ray image,
   wherein the step of applying the X-ray image information detection system to the X-ray images comprises determining at least one of an anatomy, a laterality, an orientation and a rotation of an anatomy represented within the X-ray image using the X-ray image information detection system, and
   wherein the step of providing the output from the X-ray image information detection system comprises outputting information on any fine identification/auto-rotation/correction of the rotation of the X-ray image.

2. The method of claim 1, further comprising the steps of:
   identifying an image analysis algorithm corresponding to the anatomy determined within the X-ray image; and
   transmitting the X-ray image to the corresponding image analysis algorithm.

3. The method of claim 1, further comprising the step of correcting the rotation of the X-ray image using the X-ray image information detection system if the determined rotation does not correspond to the view determined for the X-ray image.

4. The method of claim 3, wherein the step of correcting the rotation is performed automatically by the X-ray image detection system, manually by a user, or a combination thereof.

5. The method of claim 1, further comprising the step of applying one or more image check algorithms to the X-ray image after determining at least one of an anatomy, a laterality, an orientation and a rotation of an anatomy represented within the X-ray image.

6. The method of claim 5, wherein the step of applying the one or more image check algorithms comprises applying at least one of a positioning check algorithm, a pathology check algorithm, and an image quality algorithm to the X-ray image.

7. The method of claim 5, further comprising the step of applying a compatibility check algorithm to information determined by the X-ray image detection system for the X-ray image regarding the determination of the at least one of an anatomy, a laterality, an orientation, and a rotation of an anatomy represented within the X-ray image.

8. The method of claim 1 wherein the step of providing the output from the X-ray image information detection system comprises outputting information on at least one of an anatomy detected within the X-ray image, a number and type(s) of views for each detected anatomy, any coarse identification/auto-rotation/correction of the rotation of the X-ray image, an orientation and/or laterality of the anatomy within the X-ray image, and anatomical landmark segmentation information for the X-ray image.

9. The method of claim 8, wherein the step of providing the output from the X-ray image detection system further comprises providing a warning regarding the information for the X-ray image determined by the X-ray image detection system.

10. The method of claim 8, wherein the step of providing the output from the X-ray image detection system further comprises providing a digital DICOM tag representing the information for the X-ray image determined by the X-ray image detection system.

11. The method of claim 1, further comprising the step of storing the output from the X-ray image detection system in conjunction with the X-ray image.

12. The method of claim 1, wherein the X-ray image detection system is employed directly on the X-ray system.

13. The method of claim 1, wherein the X-ray image detection system is employed remotely from the X-ray system.

14. An X-ray system comprising:
    an X-ray source;
    an X-ray detector positionable in alignment with the X-ray ray source; and
    a processing unit operably connected to the X-ray source and the X-ray detector to produce X-ray images from data transmitted from the X-ray detector,
    wherein the processing unit includes an X-ray image information detection system configured to detect information regarding at least one of an anatomy, a laterality, an orientation and a rotation of an anatomy represented within the X-ray image using the X-ray image information detection system, and
    wherein the X-ray image information detection system is further configured to output information on any fine identification/auto-rotation/correction of the rotation of the X-ray image.

15. The X-ray system of claim 13, wherein the X-ray image information detection system is further configured to output information on at least one of an anatomy detected within the X-ray image, a number and type(s) of views for each detected anatomy, any coarse identification/auto-rotation/correction of the rotation of the X-ray image, an orientation and/or laterality of the anatomy within the X-ray image, and anatomical landmark segmentation information for the X-ray image.

16. The X-ray system of claim 15, wherein the X-ray image information detection system is further configured to correct the rotation of the X-ray image if the determined rotation does not correspond to the view determined for the X-ray image.

17. The X-ray system of claim 15, wherein the X-ray image information detection system is further configures to output a digital DICOM tag representing the information for the X-ray image determined by the X-ray image detection system.

18. The X-ray system of claim 14, wherein the X-ray image detection system is employed directly on the X-ray system.

19. The X-ray system of claim 14, wherein the X-ray image detection system is employed remotely from the X-ray system.

* * * * *